United States Patent [19]

Schmidt et al.

[11] Patent Number: 5,756,695

[45] Date of Patent: May 26, 1998

[54] METHODS OF SYNTHESIZING GM2

[75] Inventors: Richard Schmidt; Julio C. Castro-Palomino; Andreas Doll, all of Constance, Germany; Gerd Ritter; Lloyd J. Old, both of New York, N.Y.

[73] Assignee: Ludwig Institute for Cancer Research, New York, N.Y.

[21] Appl. No.: 602,580

[22] Filed: Feb. 16, 1996

[51] Int. Cl.⁶ ........................................ C07H 1/00
[52] U.S. Cl. ........................................ 536/18.5; 536/18.6
[58] Field of Search ........................... 536/18.5, 18.6

[56] References Cited

PUBLICATIONS

Sugimoto et al. *Carbohydr. Res.* 1986, 156, C1–C5.

*Primary Examiner*—Kathleen K. Fonda
*Attorney, Agent, or Firm*—Felfe & Lynch

[57] ABSTRACT

This invention relates to methods of producing synthetic GM2s. The methods are simple and efficient, and result in high yields of GM2s.

16 Claims, 5 Drawing Sheets

METHODS OF SYNTHESIZING GM2

FIELD OF THE INVENTION

This invention relates methods of producing synthetic GM2s. The synthetic GM2s produced by the methods of the invention have greater than 95% purity, and have the same immunoreactivity with anti-GM2 antibodies as bovine brain-derived GM2s.

BACKGROUND OF THE INVENTION

Gangliosides are a class of molecules which are glycolipids. Different gangliosides have been identified as prominent cell surface constituents of various transformed cells, including melanoma, as well as other tumors of neuroectodermal origin. See, e.g., Ritter and Livingston, et al., Sem. Canc. Biol., 2:401–409 (1991) and Oettgen, VCH Verlags Gesellschaft (Weinheim Germany 1989), both of which are incorporated herein by reference.

Gangliosides are known as mono-, di-, tri or polysialogangliosides, depending upon the degree of glycosylation with sialic acid residues. Abbreviations employed to identify these molecules include "GM1", "GD3", "GT1", etc., with the "G" standing for ganglioside, "M", "D" or "T", etc. referring to the number of sialic acid residues, and the number or number plus letter (e.g., "GT1a"), referring to the binding pattern observed for the molecule. See Lehninger, Biochemistry, pg. 294–296 (Worth Publishers, 1981); Wiegandt, Glycolipids: New Comprehensive Biochemistry (Neuberger et al., ed., Elsevier, 1985), pp. 199–260.

The monosialoganglioside GM2 has the structure:

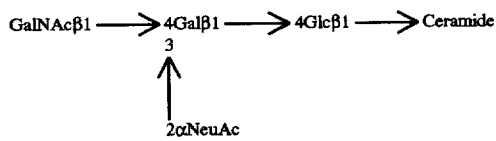

The gangliosides are prevalent cell surface markers on transformed cells, such as melanoma. This has made them attractive targets for cancer research. Livingston, et al., Proc. Natl. Acad. Sci. USA, 84:2911–2915 (1987), which is incorporated herein by reference, describe results of a vaccine based trial, wherein subjects afflicted with melanoma received, as vaccines, either whole cells which present high levels of GM2, pure GM2 or pure GM2 plus bacterial adjuvant. Attention is also drawn to Livingston, et al., J. Clin. Oncol., 12(5):1036–1044 (1994), and Irie, et al., U.S. Pat. No. 4,557,931, both of which are incorporated herein by reference, and deal with the use of GM2 as a vaccine.

There are difficulties unique to the immunology of gangliosides, which are touched upon briefly here. First, while these molecules are prevalent on transformed cells, they are also common on certain normal cells, such as neural cells. There is a risk, in administering gangliosides to a subject, that the resulting antibody response will damage normal cells. Indeed, certain autoimmune pathologies, such as Guillain-Barre' Syndrome, are characterized by autoimmune antibodies reactive with GM1 or GQ1b. See, e.g., Yuki, et al., J. Exp. Med., 178:11771–1775 (1993); Aspinall, et al., Infect & Immun., 6295) :2122–2125 (1994).

There is an additional practical problem in that highly pure gangliosides are extremely difficult to secure in amounts sufficient for immunization protocols. No practical synthetic method is presently available. As a result, gangliosides are secured via purification from tissue, such as bovine cranial tissues. Even under optimum conditions, the yields of pure gangliosides, in particular, GM2, are vanishingly small. Further, purification from mammalian tissue carries with it the risk of transmitting contaminants such as viruses, prion particles, and so forth. Alternate methodologies for securing ganglioside specific antibodies are thus highly desirable.

Due to the importance of gangliosides, it is desirable to develop a method of synthesizing high yields of pure gangliosides. The inventors of the instant application have developed novel methods of synthesizing pure GM2s, in high yields. Other methods of developing synthetic GM2s are described in Hasegawa et al., J. Carbohydrate Chemistry, 11(6):699–714 (1992) and Sugimoto et al., Carbohydrate Research, 156:C1–C5 (1986). The invention described herein develops the art in that the methods described herein are not suggested by these references.

SUMMARY OF THE INVENTION

This invention is directed to methods of synthesizing GM2. In the first method, trisaccharide compound IIIa or IIIb and glycosyl donor compound IV are glycosylated in the presence of a catalyst to obtain tetrasaccharide compound Va or Vb. The N-trichloroethyoxycarbonyl group is removed and the acetamido group is liberated from compound Va or Vb to obtain acetamino derivative compound VIa or VIb. Compound VIa or VIb is debenzylated and O-acetylated to obtain compound VIIa or VIIb, which is then transformed into GM2.

In the second method, trisaccharide compound IIIa or IIIb and glycosyl donor compound VIII are glycosylated in the presence of a catalyst to obtain compound IXa or IXb. Compound IXa or IXb is converted to acetamino derivative compound VIa or VIb. Compound VIa or VIb is debenzylated and O-acetylated to obtain compound VIIa or VIIb, which is then transformed into GM2.

In the third method, trisaccharide compound IIIa or IIIb and glycosyl donor compound X are glycosylated in the presence of a catalyst and the glycosylation product is in situ treated with zinc in acetic anhydride to obtain compound VIa or VIb. Compound VIa or VIb is debenzylated and O-acetylated to obtain compound VIIa or VIIb, which is then transformed into GM2.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein.

DETAILED DESCRIPTION OF THE INVENTION

Figure 1A:
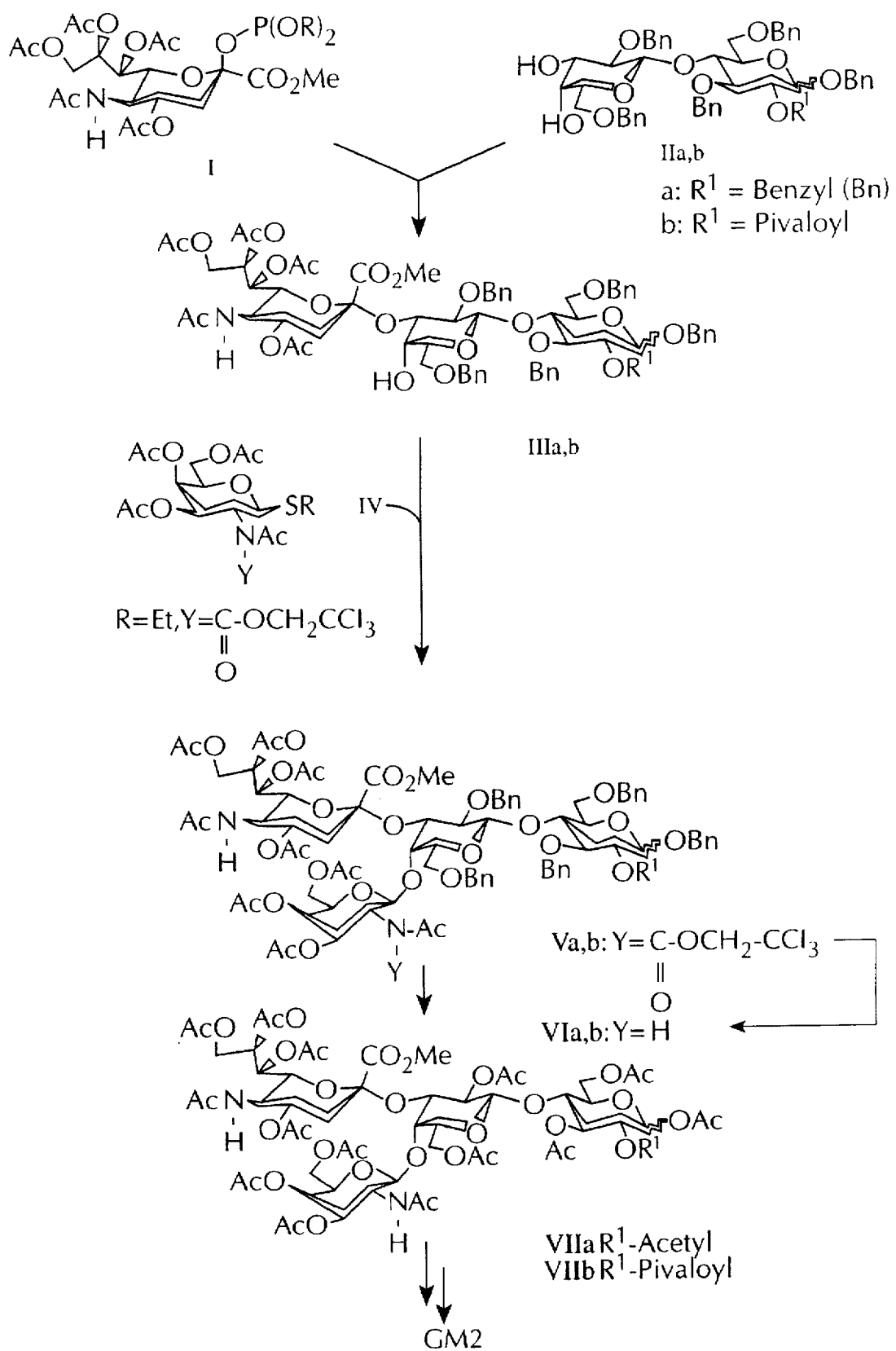
FIG. 1 is comprised of FIGS. 1A, 1B, and 1C, and represents a schematic diagram of methods and compounds used to make GM2 in accordance with the invention.

This invention is directed to methods of synthesizing GM2. In the first method, GM3 related trisaccharides (compound IIIa and IIIb, FIG. 1A, wherein, in a preferred embodiment $R^1$= benzyl or $R^1$= pivaloyl) are obtained. These compounds can be obtained using known sialyl donors (compound I (FIG. 1A) wherein R is preferably ethyl) and known glycosyl acceptors (compound II, FIG. 1A, wherein $R^1$ is preferably benzyl or pivaloyl). (See T. J. Martin et al., Glycoconjugate J., Vol. 10, p. 16–28 (1993), and Murase et al., Carbohydr. Res., Vol. 184, pp. C1–C4 (1984), which are incorporated herein by reference.) Tin(II) trifluoromethane-sulfonate, ytterbium (III) trifluoromethanesulfonate, copper (II) trifluoromethanesulfonate, silver (I) trifluoromethanesulfonate, and related metal trifluoromethanesulfonates are used as catalysts herein. These catalysts are superior to the commonly used catalyst trimethylsilyl trifluoromethanesulfonate (T. J. Martin et al., supra). Thus, higher yields of the desired α-product compound III are obtained.

Direct reaction of ethyl 3,4,6-tri-O-acetyl-2-deoxy-2-(N-trichloroethyoxycarbonyl)-acetamido-1-thio-β-D-galactopyranoside (compound IV, FIG. 1A) with compound III in the presence of N-iodosuccinimide (NIS) and trifluoromethanesulfonic acid as promoter system leads to benzyl O-(3,4,6-tri-O-acetyl-2-deoxy-2-(N-trichloroethoxycarbonyl) acetamido-β-D-galactopyranosyl)-(1-4)-{[methyl(5-acetamido-4,7,8,9-tetra-O-acetyl-3,5-dideoxy-D-glycero-α-D-galacto-2-nonulopyranosyl)onate]-(2-3)}-,2,6-di-O-benzyl-β-D-galactopyranosyl)-(1-4)-2,3,6-tri-O-benzyl- (compound Va, FIG. 1A) or -3,6-di-O-benzyl-2-O-pivaloyl-a/β-D-glucopyranoside (compound Vb, FIG. 1A), respectively. Compound Va or Vb is then subjected to removal of the N-trichloroethyoxycarbonyl group with the help of zinc in acetic acid liberating the acetamido group and furnishing benzyl O-(2-acetamido-3,4,6-tri-O-acetyl-2-deoxy-β-D-galactopyranosyl)-(1-4)-{[methyl (5-acetamido-4,7,8,9-tetra-O-acetyl-3,5-dideoxy-D-glycero-α-D-galacto-2-nonulopyranosyl)onate]-(2-3)}-(2,6-di-O-benzyl-β-D-galactopyranosyl)-(1-4)-2,3,6-tri-O-benzyl-(compound VIa, FIG. 1A) or -3,6-di-O-benzyl-2-O-pivaloyl-α/β-D-glucopyranoside (compound VIb, FIG. 1A), respectively.

Next, removal of the O-benzyl groups and ensuing treatment with acetic anhydride in pyridine under standard conditions produces the synthesis products VIIa and VIIb (FIG. 1A), which are then transformed into GM2 using known procedures (see R. R. Schmidt et al., Angew. Chem Int. Ed. Engl., Vol. 25, p. 725–726 (1986) and Liebigs Ann. Chem. p. 449–464 (1994) which are incorporated herein by reference). Reactions of IIIa and IIIb with known methyl 3,4,6-tri-O-acetyl-2-(N-acetyl)acetamido-2-deoxy-1-thio-β-D-galactopyranoside, having a more reactive N-acyl group, as glycosyl donor (see J. C. Castro-Palomino, et al, Tetrahedron Lett. Vol. 36, p. 6871–6874 (1995)) led mainly to N/O-acetyl transfer, thus preventing high product yields of compounds Va and Vb. Therefore, compounds IVa and IVb and structurally related compounds, having selectively removable N-carbonyl moieties (for instance, benzyloxycarbonyl, allyloxycarbonyl, etc.) are ideal glycosyl donors for high glycoside yields at this hindered 4-hydroxy group of the galactose moiety. Additionally, they are accessible to direct liberation of the 2-acetamido group at the required N-acetylgalactosamine moiety without leading to the intermediacy of a free amino group.

Figure 1B:
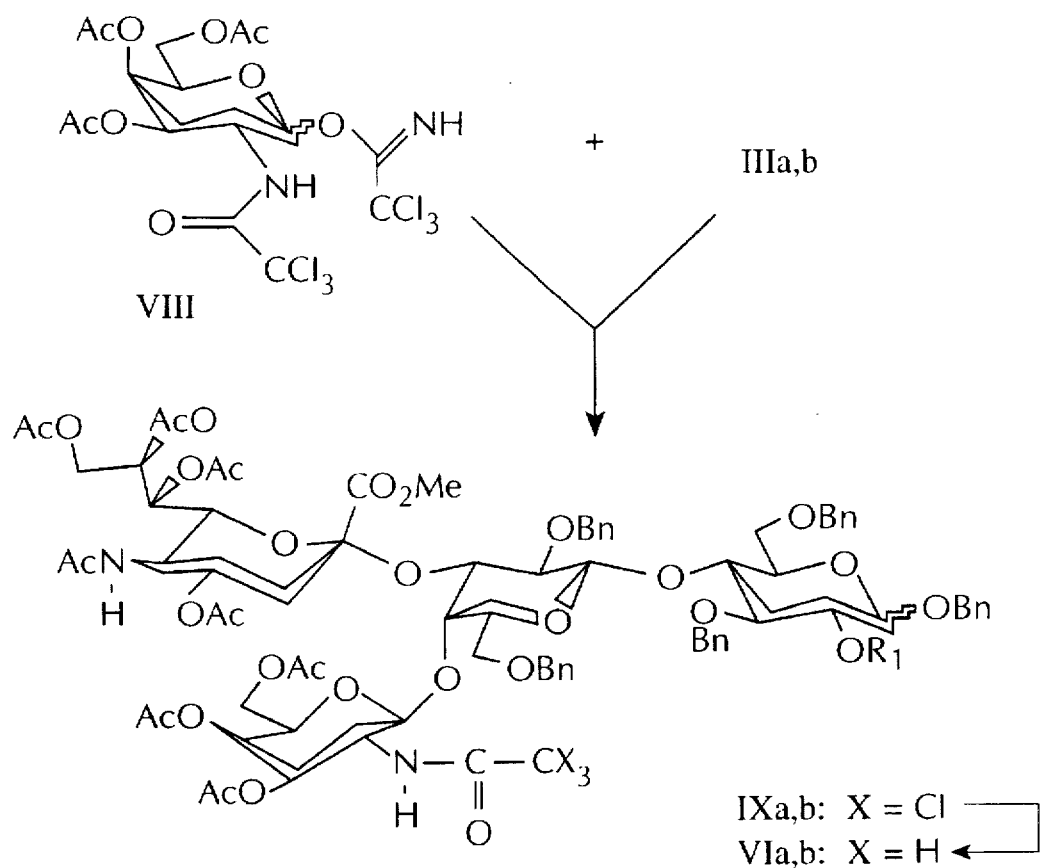

A second method of synthesizing GM2 calls for the transformation of compound III into compound VI. This method consists of the use of O-(3,4,6-tri-O-acetyl-2-deoxy-2-trichloroacetamido-α-D-galactopyranosyl) trichloroacetimidate (compound VIII, FIG. 1B) as glycosyl donor, for instance, with IIIa or IIIb as glycosyl acceptors having the low reactive 4-hydroxy group of the galactose moiety. Thus, benzyl O-(3,4,6-tri-O-acetyl-2-deoxy-2-trichloroacetamido-β-D-galactopyranosyl)-(1-4)-{[methyl (5-acetamido-4,7,8,9-tetra-O-acetyl-3,5-dideoxy-D-glycero-α-D-galacto-2-nonulopyranosyl)onate]-(2-3)}-(2,6-di-O-benzyl-β-D-galactopyranosyl)-(1-4)-2,3,6-tri-O-benzyl- (compound IXa, FIG. 1B) or -3,6-di-O-benzyl-2-O-pivaloyl-α,β-D-glucopyranoside (compound IXb, FIG. 1B), respectively, are obtained in good yields. Reductive removal of the chlorine atoms in the trichloroacetamido group, for instance, with tributyltin hydride, leads directly to the desired acetamido derivatives VIa and VIb. Thus, it is exhibited that any strongly electron attractive group at the amino group of the galactosamine moiety which, after the glycosylation step, can be directly transformed into an N-acetyl group, will serve this purpose. This is exhibited in a third method, where the electron attractive N-trichloroethoxycarbonyl group is employed to support the glycosylation reaction and then replaced in situ by an N-acetyl group with zinc in acetic anhydride.

In the instant invention, new catalysts are used for the attachment of the Neu5Ac residue to the lactose moiety, thus providing α(2–3)-connected GM3 type intermediates. The GalNAc residue is attached at the low reactive 4-OH group of the Gal moiety to obtain GM2-tetrasaccharide. Methods with lead in the deprotection steps to free amino groups (for instance, the azido or the phthalimido group) frequently result in low yields due to difficulties in the removal of the protecting groups, and/or in side reactions (lactam formation with the ester group of the Neu5Ac residue). The invention described herein provides methods which allow for a readily removable auxiliary group at the 2-acetamido group or for a substitute of the 2-acetamido group of the GalNAc residue. Thus, the required enhancement of the glycosyl donor properties with the direct liberation of the 2-acetamido group is gained without resorting to the free amine and its subsequent N-acetylation.

EXAMPLE 1

In order to prepare II$^3$NeuAcGgOse$_3$Cer, referred to herein as GM2, compound I (R=ethyl) and compounds IIa, b were prepared as described by T. J. Martin et al., Glycoconjugate J. 1993, supra. In order to obtain compounds II a and b, a solution of donor I (1 mmol) and acceptor III (1.5 mmol) in dry acetonitrile (5 mL) was cooled to −40° C. Under a nitrogen atmosphere the catalyst (0.15 mmol) tin (II) trifluoromethanesulfonate) was added. After 1 hour, the solution was neutralized with triethylamine and evaporated in vacuo. The residue was purified by flash chromatography on silica gel with toluene-acetone (3:1) as eluent to give compound III in 65% yield. For NMR data, see T. J. Martin et al., Glycoconjugate J. 1993, supra.

For compound IV, Y can be any readily removable oxycarbonyl, thiorcarbonyl or aminocarbonyl derivative, including, but not limited to, 2,2,2-tribromoethoxycarbonyl, allyloxycarbonyl, benzyloxycarbonyl, 4-nitrophenylethoxycarbonyl or trichloromethylthiocarbonyl. Glycosyl donor compound IV (R=methyl, Y=trichloroethoxycarbonyl) was obtained via the following procedure:

1,3,4,6-Tetra-O-acetyl-2-amino-2-deoxy-β-D-galactopyranose was prepared as described by R. Bergmann et al., *Chem. Ber.* Vol. 64, p. 977–979 (1991). This crystalline amine (3.2 g, 9.21 mmol) was dissolved at 0° C. in anhydrous $CH_2Cl_2$ (30 mL), and Hünig's base (1.7 mL; 18.8 mmol) and trichloroethoxycarbonyl chloride (1.5 mL, 11.05 mmol) were added successively. The mixture was stirred for 30 minutes and then diluted with $CH_2Cl_2$ (20 mL), washed with water, saturated aqueous $NaHCO_3$ solution and water, dried with $MgSO_4$ and concentrated. The residue was eluted from a column of silica gel with 2:1 hexane: ethyl acetate to give 1,3,4,6-tera-O-acetyl-2-deoxy-2-trichloroethoxycarbonylamino-β-D-galactopyranoside (4.9 g, 97%). The ethylthio group was introduced in this compound following a procedure by M. Schultz et al, *Tetrahedron Asymmetry* Vol. 4, 1205–1250 (1993), to give ethyl 3,4,6-tri-O-acetyl-2-deoxy-1-thio-2-trichloroethyoxycarbonylamino-β-D-galactopyranoside.

For its transformation into compound IV, the following procedure was applied: A mixture of ethyl 3,4,6-tri-O-acetyl-2-deoxy-1-thio-2-trichloroethoxycarbonylamino-β-D-galactopyranoside (1.74 g, 3.31 mmol), $Ac_2O$ (0.78 mL, 8.28 mmol), Hünig's base (0.56 mL, 3.31 mmol) and N,N-dimethylaminopyridine (0.4 g, 3.31 mmol) was stirred for two days at room temperature. The solvent was removed in vacuo and the residue was purified by flash chromatography with toluene/ethyl acetate (6:1) to produce compound IV (1.70 g, 3.00 mmol, 91%).-$[a]_D^{22}$−51.2 (c=1, $CHCL_3$); $R_f$ 0.42 (toluene/ethyl acetate, 4:1).

For the glycosylation of III with IV to obtain tetrasaccharides compounds Va and b, the following general procedure was applied: compound III (0.34 mmol) and compound IV (401 mg, 0.68 mmol) were dissolved in dichloromethane (5 mL). N-iodosuccinimide (168 mg, 0.75 mmol) and trifluoromethanesulfonic acid (0.67 µL, 0.075 mmol) were added successively and the mixture was stirred for 30 minutes until TLC (toluene/acetone, 3:1) indicated complete reaction. The mixture was diluted with dichloromethane and washed with saturated aqueous $NaHCO_3$, 1M $Na_2S_2O_3$ solution and water, dried with $MgSO_4$ and concentrated. The residue was purified by silica gel column chromatography (toluene/acetone, 3:1) to afford compound V (61%).

For the immediate transformation into acetamido derivative compounds VIa and b, the following procedure was applied: A solution of the tetrasaccharide compound V (0.18 mmol) in acetic acid (10 mL) was vigorously stirred with 150 mg of freshly activated zinc powder for 4 hours. The suspension was filtered through Celite and evaporated in vacuo. The residue was purified by silica gel column chromatography with toluene/acetone, 3:1 to afford compound VI (90%).

The structures of these compounds could be unequivocally assigned: compound VIa has physical data in accordance with material obtained via a different route (see: M. Sugimota et al., *Carbohydr. Res.* Vol. p. 56, C1–C5 (1986)). The structure of compound VIb followed from the $^1H$ NMR data (600 MHz, $CDCL_3$); δ=1.73–2.19 (9×s, 27 H, 9×$CH_3$), 1.18 (s, 9 H,tBu), 2.11 (dd, 1H, $3c_a$-H), 2.22 (dd, 1 H, $3c_e$-H), 3.15 (m, 1H, 6a-H), 3.29 (m, 1H, 6a-H), 3.39–3.47 (m, 3 H, 5A–H+2b–H+6b–H), 3.66 (dd, 1 H, $J_{2,3}$=$J_{3,4}$=10 Hz, 3a-H), 3.72 (m, 2H, 6b-H+4b-H), 3.79 (dd, 1 H, $J_{2,3}$=9.8 Hz, $J_{3,4}$=1.4 Hz, 3b-H), 3.89 (s, 3H, $OCH_3$), 3.90–4.70 (m, 14 H, 5×$CH_2Bn$+2×6d-H+2×9c-H), 4.02 (dd, 1H, 5c-H), 4.37 (d, 1 H, $J_{1,2}$=9.8 Hz, 1b-H), 4.47 (d, 1 H, $J_{1,2}$=10 Hz, 1a-H), 4.50 (dd, 1H, 2d-H), 4.89 (d, 1H, $J_{1,2}$=9.3 Hz, 1d-H), 5.08 (dd, $J_{1,2}$=$J_{2,3}$=10 Hz, 1 H, 2a-H), 5.13 (dd, 1 H, $J_{2,3}$=9.3 Hz, $J_{3,4}$=1.8 Hz, 3d-H), 5.40 (dd, 1 H, $J_{3,4}$=1.8 Hz, $J_{4,5}$=0.8 Hz, 4d-H), 5.15–5.32 (m, 2H, 7c-H+8c-H).

Debenzylation of compounds VIa and b and subsequent O-acetylation to produce compounds VII a and b was performed using standard procedures. A mixture of compound VIa (85 mg, 51 µmol) and 10% Pd-C (15 mg) in $MeOH$-$CH_3COOH$ (8 mL, 5:1) was stirred for 2 hours at room temperature under $H_2$. After filtration, the solution was concentrated. Without purification, a mixture of the residue, acetic anhydride (1 mL), pyridine (1 mL), and 4-dimethylaminopyridine (12 mg, 0.10 mmol) was stirred overnight at room temperature and then concentrated. The residue was chromatographed on silica gel with 5:1 toluene-acetone to give compound VIIa (66 mg, 94%).-$[a]_D$+1.6° (c=1, $CHCl_3$); $R_f$ 0.32, 95:5, $CHCl_3$-MeOH. Compound VIIa is identical with material obtained via a different route. Compound VII can then be transformed into GM2 using standard techniques known to those skilled in the art (see, for example, Schmidt et al., *Agnew. Chem. Int. Ed. Engl.*, Vol. 25, pp. 725–726 (1986) and *Liebigs Ann. Chem.*, pp. 449–464 (1994), which are incorporated herein by reference).

EXAMPLE 2

A second method for the synthesis of compound VI is provided. This method requires the preparation of glycosyl donor compound VIII. This was performed via the following procedures starting from galactosamine: Trichloroacetyl chloride (3.88 mL, 34.8 mmol) was added dropwise at room temperature within 30 minutes to a vigorously stirred solution of D-galactosamine hydrochloride (5 g, 23.4 mmol) and $NaHCO_3$ (5.84 g, 69 mmol) in water (46 mL). The mixture was stirred for 1 hour, neutralized with 1M HCl, concentrated and dried in vacuo. The residue was stirred for 3 hours at 0° C. with MeOH (50 mL). The salts were filtered off, and the filtrate was concentrated to give a mixture of N-trichloroacetyl-D-galactosamine and D-galactosamine (quantitive yield); $R_f$0.20 (toluene/acetone, 4:6).

A solution of this crude product (10 g) in acetic anhydride (25 mL) and pyridine (1 mL) was stirred for 3 hours at room temperature, and then concentrated. The residue was chromatographed on silica gel with 7:1 toluene-acetone to give 1,3,4,6-tetra-O-acetyl-2-deoxy-2-trichloroacetamido-α,β-D-galactopyranose as a white solid (1.85 g, 30%). β-isomer: $[a]_D$+3.9°(c=1, $CHCl_3$); $R_f$ 0.85 in 95:5 $CHCL_3$/MeOH.

The following procedure gave a much higher yield of this material: A solution of 1,3,4,6-tetra-O-acetyl-2-deoxy-2-amino-β-D-galactopyranose (150 mg, 0.43 mmol), and 4-dimethylaminopyridine (5 mg, 0.04 mmol) in $CH_2Cl_2$ was cooled to 0° C. Trichloroacetyl chloride (53 µL, 0.48 mmol) and N,N-diisopropylamine (83 µL, 0.48 mmol) were added. The mixture was stirred at room temperature for 3 hours, and then concentrated. The residue was chromatographed on silica gel with 7:1 toluene/acetone to give 170 mg, 80%. β-Isomer $^1H$ NMR (250 MHz, $CDCl_3$): 2.16, 2.10, 2.03, 1.97 (4 s, 12 H, 4 Ac), 4.04 (dd, 1H, $J_{5,6}$=3.5 Hz, 5-H), 4.13 (dd, 2H, $J_{6a,6b}$=11.2 Hz, 6A-H, 6B-H), 4.42 (ddd, 1 H, 2-H), 5.25 (dd, 1H, $J_{2,3}$=11.2 Hz, $J_{3,4}$=1.3 Hz, 3-H), 5.37 (d, 1 H, $J_{4,5}$=2.9 Hz, 4-H), 5.84 (d, 1H, $J_{1,2}$=8.8 Hz, 1-Hβ), 7.08 (d, 1H, J=9.6 Hz, NH).

Transformation into compound VIII was performed as follows: A solution of 1,3,4,6-tetra-O-acetyl-2-deoxy-2- trichloroacetamide-a,β-D-galactopyranose (1.73 g, 3.5 mmol) and hydrazine acetate (355 mg, 3.9 mmol) in DMF (20 mL) was stirred for 2 hours at 0° C., and then diluted with EtOAc (60 mL), washed with saturated aqueous NaCl and water, dried with $MgSO_4$, and concentrated. A mixture of the residue, trichloroacetonitrile (3.35 mL, 33.4 mmol) and DBU (0.1 mL, 0.7 mmol) in $CH_2Cl_2$ (15 mL) was stirred for 30 minutes at room temperature, and then concentrated. The residue was chromatographed on silica gel with 2:1 petroleum ether/ethyl acetate containing 0.1% of triethylamine to give compound VIII (1.04 g, 50%). $[a]_D+63°$ (c=1, $CHCl_3$); $R_f$ 0.62 in 2:1 petroleum ether/ethyl acetate and 0.1% $NEt_3$ $^1H$ NMR (250 MHz, $CDCl_3$): 2.19, 2.02, 2.01 (3 s, 9 H, 3 Ac), 4.06 (dd, 1 H, 6B-H), 4.17 (dd, 1 H, $J_{6a,6b}$=11.3 Hz, 6A-H), 4.35 (dd, 1 H, $J_{5,6}$=6.9 Hz, 5-H), 4.70 (ddd, 1 H, 2-H), 5.39 (dd, 1H, $J_{2,3}$=11.3 Hz, $J_{3,4}$=3.1 Hz, 3-H), 5.51 (dd, 1H, $J_{4,5}$<1 Hz, 4-H), 6.49 (d, 1H, $J_{1,2}$=3.6 Hz, 1-Ha), 6.81 (d, 1H, $J_{9,1}$ Hz, NH), 8.81 (s, 1 H, C=NH). Compound VIII contains a trichloroacetyl group, which can be replaced by any structurally related electron withdrawing group including, but not limited to, tribromoacetyl or trifluoroacetyl.

Reaction of glycosyl donor compound VIII with acceptor compound IIIa or b to afford compound IX was performed as described in Example 1 for compound IIIa. A mixture of compound VIII (200 mg, 0.34 mmol), compound IIIa (228, 0.17 mmol) and 4 Å molecular sieves in $CH_2Cl_2$ (8 mL) was stirred for 1 hour at room temperature under Ar, and then cooled to 0° C. Trimethylsilyl trifluoromethanesulfonate (15 μL, 84 μmol) was added, and the mixture was stirred at room temperature for 2 hours. Triethylamine (0.1 mL) was added and the mixture was diluted with $CH_2Cl_2$, filtered and concentrated. The residue was chromatographed on silica gel with 7:1 toluene/acetone to give compound IXa (222 mg, 74%). $[a]_D+3°$ (c =0.33, $CHCl_3$); $R_f$ 0.27 toluene/acetone, 4:1.

Conversion into known compound VIa was performed as follows: A solution of compound IXa (130 mg, 73 μmol), tributylstannane (0.29 mL, 1.09 mmol), and azoisobutyronitrile (3 mg) in benzene (8 mL) was stirred for 1 hour under Ar and then heated under reflux for 2 hours, cooled, and concentrated. The residue was chromatographed on silica gel with 7:1 toluene/acetone to give compound VIa (100 mg, 81%), which was identical with the above described material; $[a]_D$- 6.8° (c=1, CHCl); $R_f$ 0.48 95:5 $CHCl_3$-MeOH. Compound VIa or VIb is then used to produce compound VIIa or VIIb, which is then transformed into GM2 using standard techniques known to those skilled in the art.

EXAMPLE 3

Figure 1C:
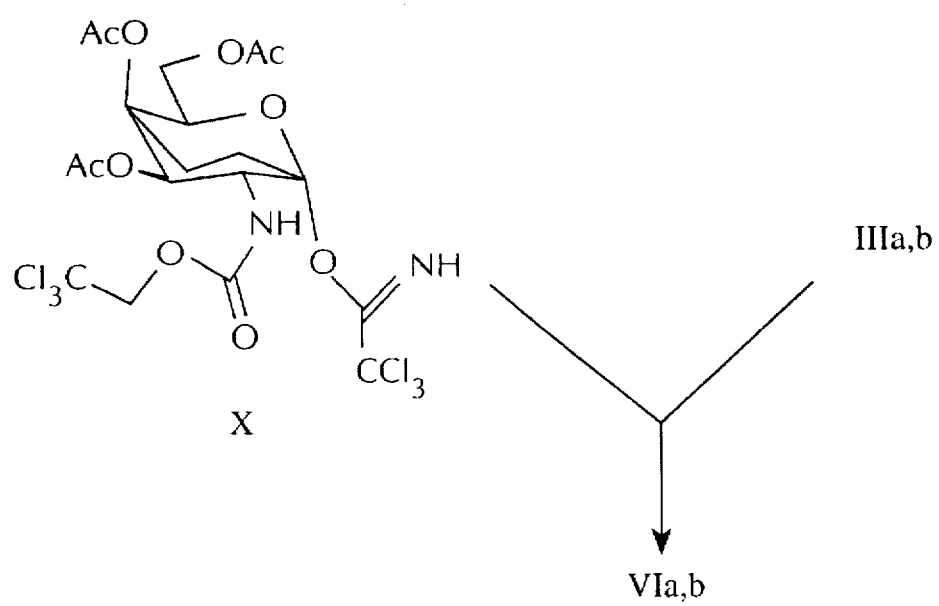

A third method for the synthesis of compound VI is provided. This method requires the preparation of glycosyl donor X (FIG. 1C). This was performed as follows: A solution of 1,3,4,6-tetra-O-acetyl-2-deoxy-2-trichloroethoxycarbonylamino-β-D-galactopyranoside (see Example 1) (3 g, 5.73 mmol) and hydrazine acetate (0.6 g, 6.31 mmol) was stirred for 20 minutes at room temperature, and then diluted with EtOAc (100 mL), washed with water, saturated aqueous $NaHCO_3$, and water, dried ($MgSO_4$), and concentrated. A mixture of the residue, trichloroacetonitrile (4 mL, 40 mmol), and DBU (0.15 mL, 1 mmol) in $CH_2CL_2$ (20 mL) was stirred for 45 minutes at room temperature, then concentrated. The residue was purified by column chromatography on silica gel (80 g) with 3:1 hexane-EtOAc containing 0.1% of $Et_3N$ to give compound X (3.05 g, 93.1%). $[a]_D+64$ (c 1, $CHCl_3$); $^1HNMR$ ($CDCl_3$): 6.45 (d, 1 H, J $_{1,2}$=3.8 Hz, H-1), 8.81 (s, 1 H, C=NH), 5.51 (dd, 1 H, $J_{3,4}=J_{4,5}$, 1.1 Hz, H-4), 5.42 (d, 1 H, J=8.5 Hz, NH), 5.28 (dd, 1 H, $J_{2,3}$=10 Hz, J $_{3,4}$ =1.1 Hz, H-3), 4.72 (dd, 2 H, $CH_2CCl_3$), 4.53 (m, 1 H, H-6'), 4.38 (m, 1 H, H-6), 4.00–4.25 (m, 2 H, H-2 +H-5), 2.00–2.13 (3×s, 9 H, 3×$CH_3$-C. Compound X contains a 2,2,2-trichloroethoxycarbonyl group, which can be replaced by any structurally related, electron withdrawing group including, but not limited to, 2,2,2-tribromoethoxylcarbonyl, 2,2,2-trifluoroethoxycarbonyl or 4-nitrophenylethoxycarbonyl.

A mixture of imidate X (120 mg, 0.192 mmol), acceptor IIIb (150 mg, 0.128 mmol) and activated 4 Å molecular sieves (200 mg) in anhydrous dichloromethane (5 mL) was stirred for 1 hour at room temperature under dry Ar. Trimethylsilyl triflate (0.35 μL, 0.0192 mmol) was added, and the mixture was stirred for 4 hours. $Et_3N$ (0.1 mL) was added, and the mixture was diluted with $CH_2Cl_2$ (25 mL), filtered, and concentrated. The residue was dissolved in a mixture of $Ac_2O$: AcOH (5:1, 6 mL) and zinc powder (200 mg) was added. The mixture was stirred 16 hours at room temperature and then filtered and concentrated in vacuo. Column chromatography of the residue afforded VIb (152.7 mg, 78%). Combined VIb can be used to produce GM2, as described above.

EXAMPLE 4

The purity of the synthetic GM2 obtained by the procedure described in Example 1 was analyzed. The GM2 was subjected to thin layer chromatography utilizing techniques known to those skilled in the art. The GM2 was visualized with resorcinol/HCl and iodine vapor as indicated in the brief description of the figures.

Figure 2:
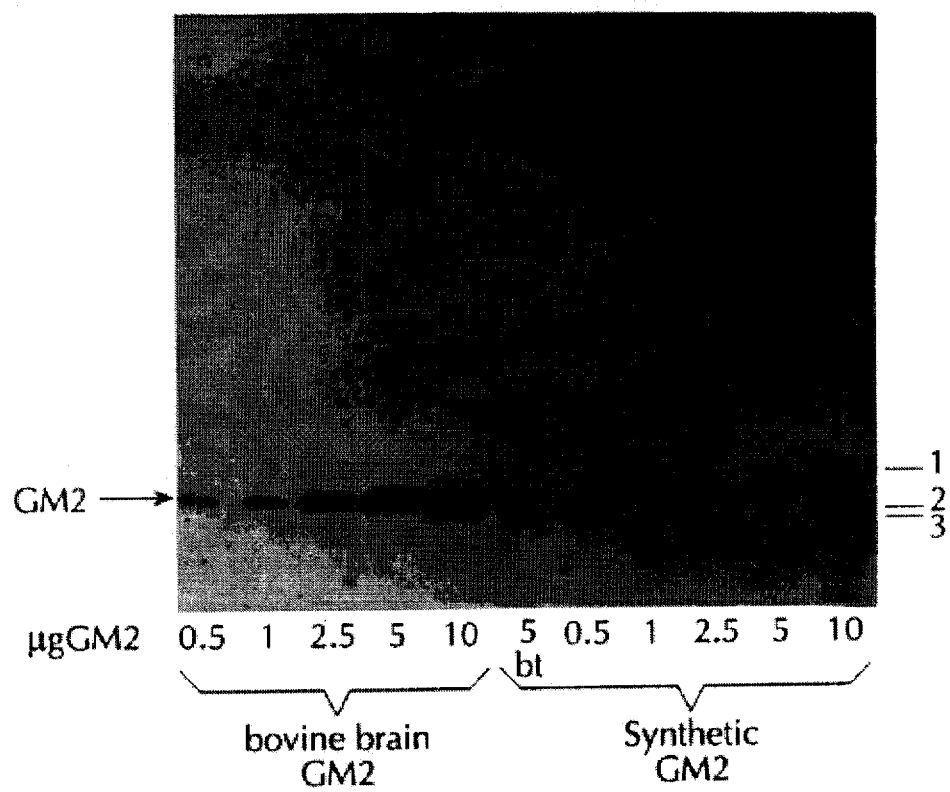
FIG. 2 represents thin-layer chromatography of the synthetic GM2 of the invention, stained with resorcinol for sialic acid containing compounds.

The synthetic GM2 contained one major band, which was resorcinol and orcinol positive. The synthetic GM2 co-migrated with bovine brain-derived GM2. In addition, three major bands were detectable after staining with orcinol and resorcinol in the lanes containing 5 and 10 μg synthetic GM2. One band migrated slightly faster, and two bands migrated slightly slower than the main GM2 band (see FIG. 2).

Figure 3:
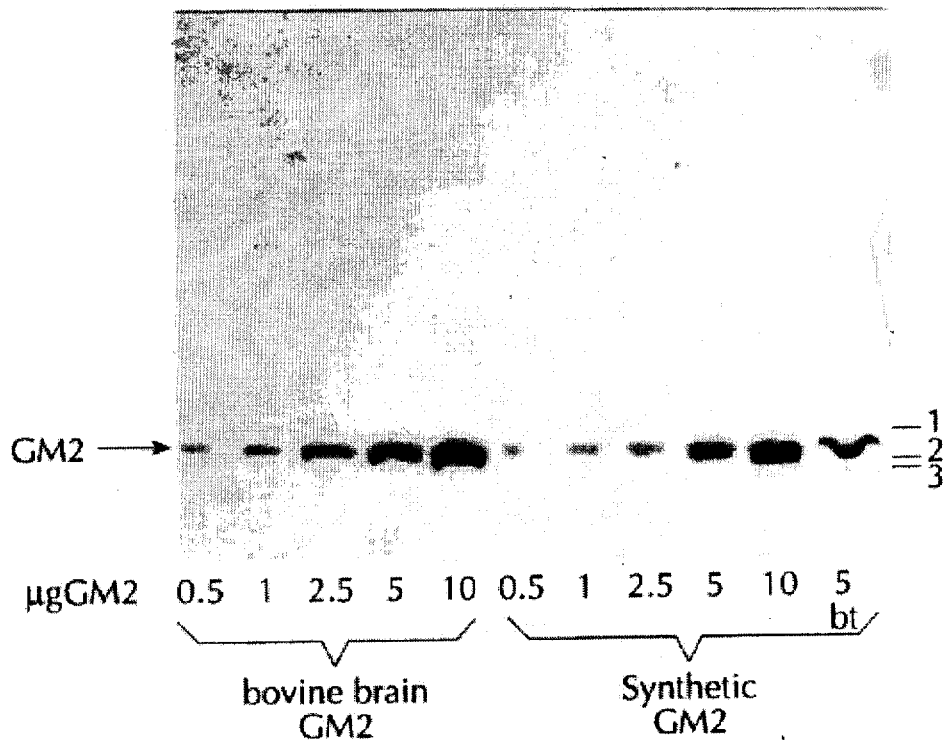
FIG. 3 represents thin-layer chromatography of the synthetic GM2 of the invention, stained with iodine vapor for lipid containing compounds.

These bands were also detectable after mild base treatment of the synthetic GM2 before thin layer chromatographic separation. Base treatment comprised treatment with 0.05 M NaOH in MeOH, at 50° C., for one hour. In addition, after staining with iodine vapor, only the main GM2 band was detectable (see FIG. 3).

The purity of the GM2 synthesized by the method described in Example 1 was found to be greater than 95%, as determined by thin layer chromatography.

With regard to the purity determination, the purity of the final product in the described process is dependent upon the purity of the starting materials. In the data described herein, the 95% would be improved, perhaps to 99%, if practical starting materials of higher purity, e.g., fatty acids with 99% higher purity, were available. Also, the term "GM2" actually refers to a backbone structure, and while the glycoside chains which are described are constant, there is a certain amount of variability possible because of natural variability in fatty acid composition of the molecules. Hence, it is better to refer to GM2 in the plural ("GM2s"), or to "a family of molecules, all of which possess the GM2 backbone structure".

EXAMPLE 5

The antigenicity of the GM2 synthesized by the method described in Example 1 was compared with the antigenicity of bovine brain-derived GM2. To do this, the synthetic GM2 was tested by ELISA for reactivity with various GM2 antisera.

Figure 4:
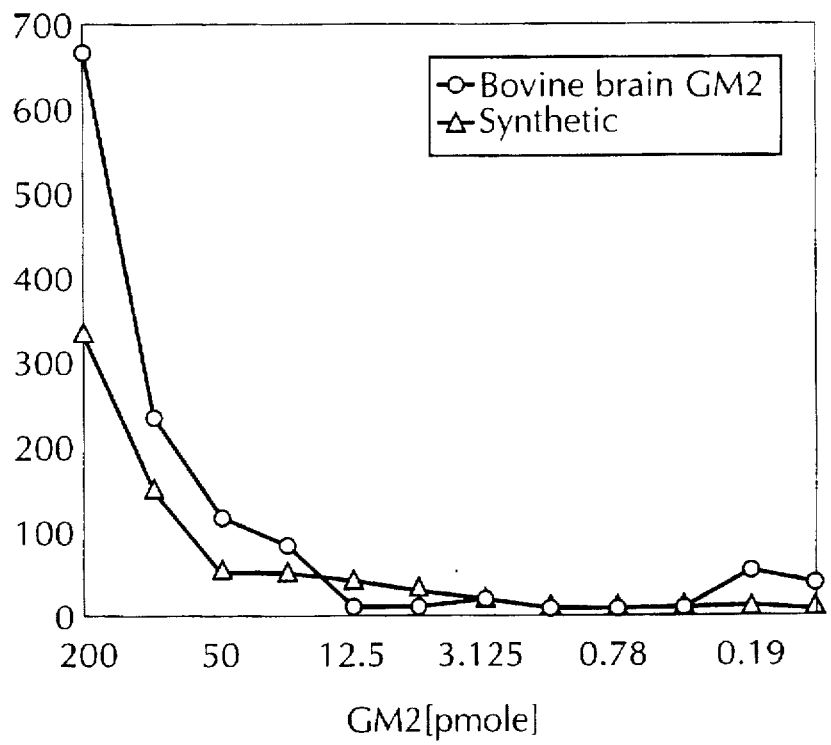
FIG. 4 represents the immunoreactivity of the synthetic GM2 of the invention and bovine brain-derived GM2 with mAb 10.11, by ELISA.
Figure 5:
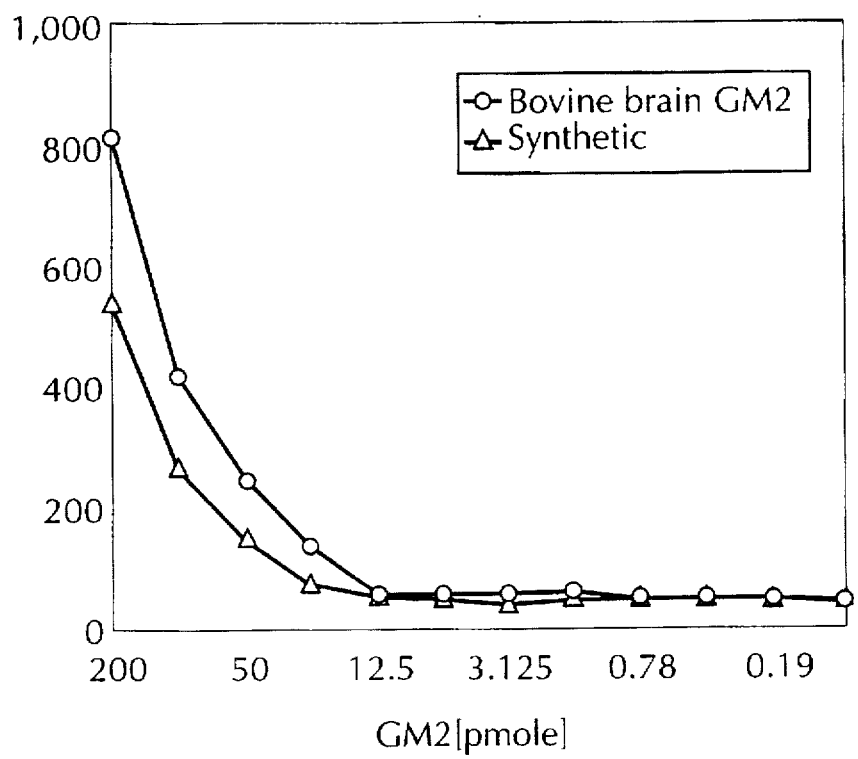
FIG. 5 represents the immunoreactivity of the synthetic GM2 of the invention and bovine brain-derived GM2 with mAb 45.114, by ELISA.
Figure 6:
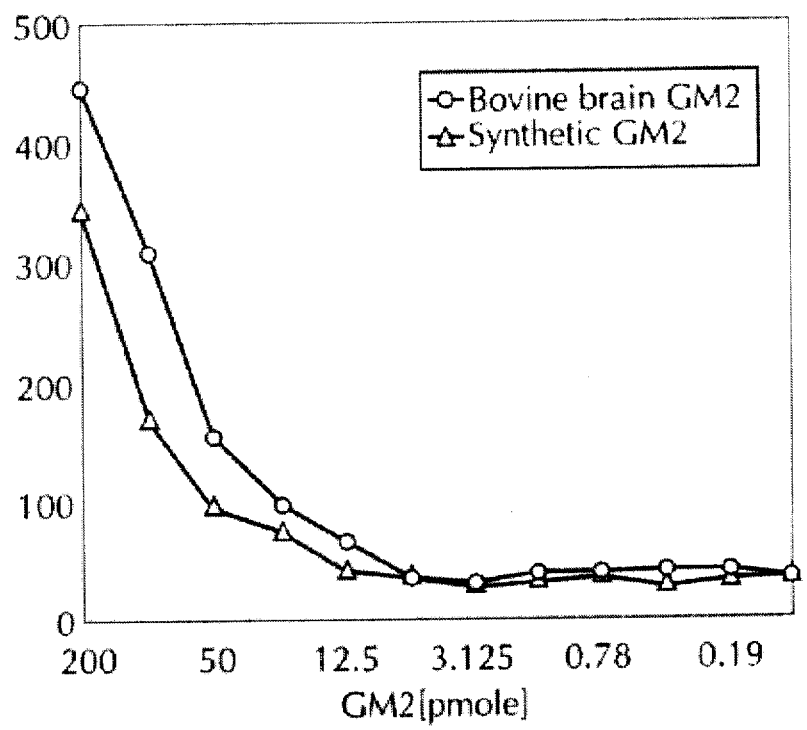
FIG. 6 represents the immunoreactivity of synthetic GM2 of the invention and bovine brain-derived GM2 with sera obtained from a melanoma patient which had been vaccinated with bovine brain-derived GM2.

To perform the ELISA, antibody titration and GM2 antigen (both synthetic and bovine brain-derived) titration were performed. The synthetic GM2 was recognized by three different GM2-reactive antisera. These antisera included murine monoclonal antibody 10.11 (FIG. 4), human monoclonal antibody 45.114 (FIG. 5), and sera from a melanoma patient which was immunized with a vaccine containing bovine brain-derived GM2 (FIG. 6).

Table 1, below, shows that the synthetic GM2 and the bovine brain-derived GM2 were recognized by the same antibodies by ELISA. Specifically, both synthetic and bovine brain-derived GM2 were recognized by monoclonal antibody 10.11, antibody 45.114, and patient sera immunized with a vaccine containing bovine brain-derived GM2. Neither the synthetic GM2 nor the bovine brain-derived GM2 was recognized by monoclonal antibodies R24 (which is an anti-GD3 monoclonal antibody) or F31, a glycolipid-recognizing antibody. Similarly, neither synthetic GM2 nor bovine brain-derived GM2 were recognized by sera from a patient which had not previously been immunized with a vaccine containing bovine brain-derived GM2.

TABLE 1

REACTIVITIES OF BOVINE BRAIN AND SYNTHETIC GM2 WITH VARIOUS ANTISERA BY ELISA

| ANTISERUM | BOVINE BRAIN GM2 TITER | SYNTHETIC GM2 (C18:0) |
|---|---|---|
| anti-GM2 | | |
| mAb 10.11 (mIgM) | >0.39 µg/ml | >0.39 µg/ml |
| mAb 45.114 (hIgM) | 1:4 | 1:8 |
| pat. serum (bovine brain GM2 vaccine) | 1:3200 | 1:3200 |
| anti-GD3 | | |
| mAb R24 (mIgG) | — | — |
| others | | |
| mAb F31 (mIgM) | — | — |
| pat. serum neg. pool (IgG) | — | — |

EXAMPLE 6

Figure 7:
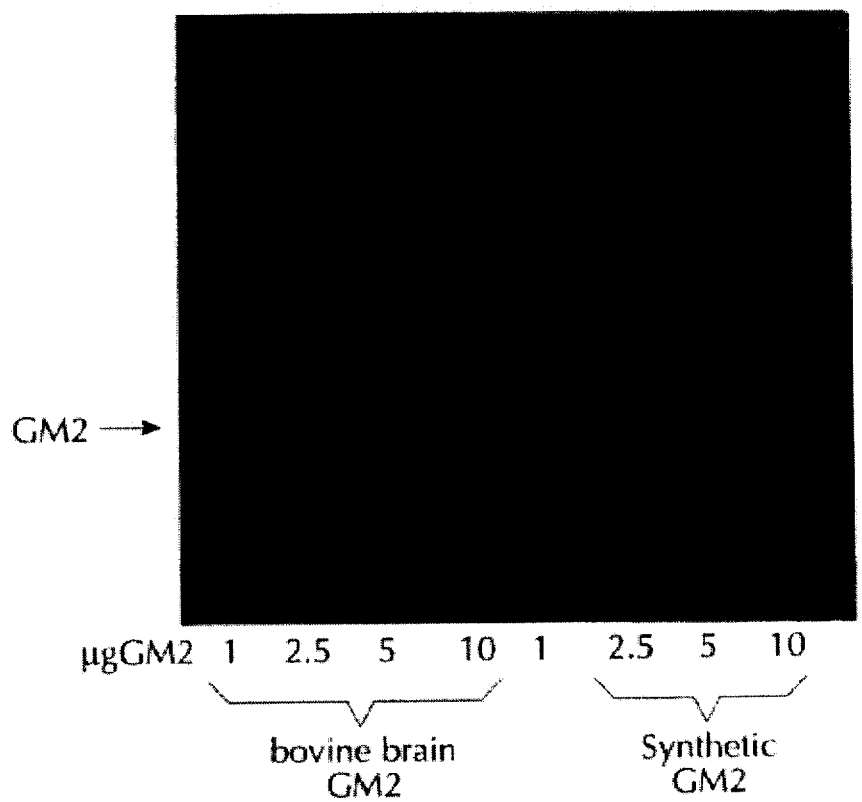
FIG. 7 represents immunoreactivity, by immune thin-layer chromatography, of the synthetic GM2 of the invention and bovine brain-derived GM2 with mAb 10.11.

The antigenicity of synthetic GM2 was compared with the antigenicity of bovine brain-derived GM2 utilizing immune thin-layer chromatography techniques known to those skilled in the art. Monoclonal antibody 10.11 (FIG. 7) was used in the chromatography.

In the synthetic GM2 preparation, one main band and two minor bands were immunoreactive with monoclonal antibody 10.11. The main band co-migrated with bovine brain-derived GM2, while both minor bands migrated slightly faster than the main GM2 band (see FIG. 7). The two minor bands which were immunoreactive with the anti-GM2 monoclonal antibodies are likely all GM2 species, which differ in ceramide composition from the major band, which contains C18:0 and d18:1. No band migrating below the main GM2 band stained specifically with monoclonal antibody 10.11.

EXAMPLE 7

Rabbits were immunized with either synthetic GM2 obtained by the method described in Example 1 or bovine brain-derived GM2 in order to induce the production of anti-GM2 antibodies. The rabbits were immunized four times at three week intervals with 200 µg GM2 for the first two immunizations and 100 µg GM2 for subsequent injections. Freund's adjuvant was utilized. After three months, two additional immunizations, at three week intervals, were given.

Sera from the immunized animals was tested for immunoreactivity. It was found that sera from both synthetic GM2-immunized rabbits and bovine brain-derived GM2-immunized rabbits had low titers of IgM and IgG anti-GM2 antibodies. Both sera had the same low levels of immunogenicity. This indicates that the synthetic GM2 and the bovine brain-derived GM2 are not distinguished by the immune system.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A process for making a monosialoganglioside compound of formula:

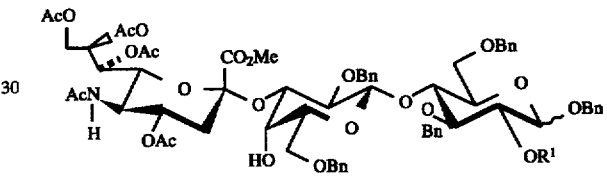

comprising reacting a compound of formula:

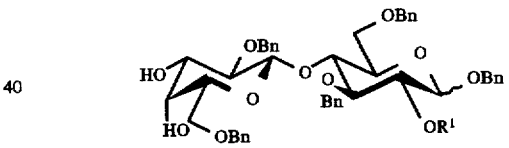

wherein R¹ is benzyl or pivaloyl; with a compound of formula:

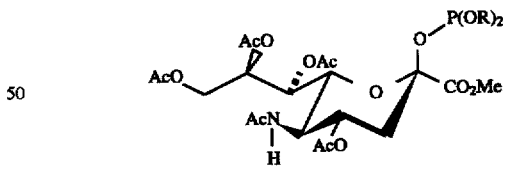

wherein R is ethyl, in the presence of a catalyst, to form said monosialoganglioside compound.

2. The process of claim 1, wherein said catalyst is a trifluoromethanesulfonate.

3. The process of claim 2, wherein said trifluoromethanesulfonate is a metal trifluoromethanesulfonate.

4. The process of claim 3, wherein said metal trifluoromethanesulfonate is tin (II) trifluoromethanesulfonate, ytterbium (III) trifluoromethanesulfonate, copper (II) trifluoromethanesulfonate, or silver (I) trifluoromethanesulfonate.

5. A process for making monosialoganglioside GM2, comprising:

(a) reacting a compound of formula:

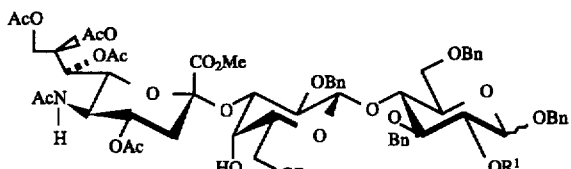

wherein R¹ is benzyl or pivaloyl, with a compound of formula:

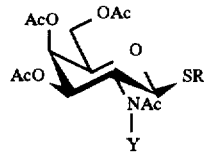

wherein R is ethyl, and Y is an oxycarbonyl, a thiocarbonyl or an aminocarbonyl, in the presence of a catalyst, to form:

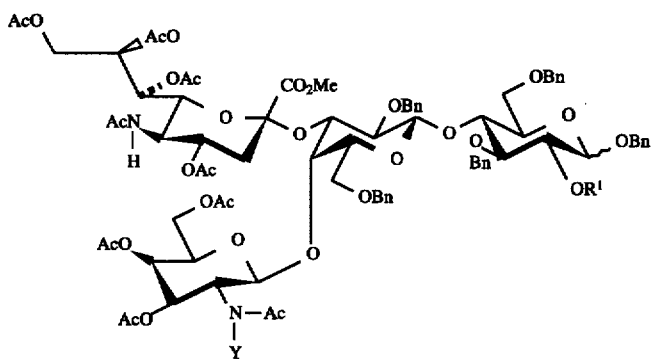

(b) removing the Y moiety from the compound formed in (a), and replacing it by a hydrogen atom;
(c) removing any O-benzyl groups from the compound formed in (b);
(d) O-acetylating the compound formed in (c); and
(e) transforming the compound formed in (d) to monosialoganglioside GM2.

6. The process of claim 5, wherein Y is 2,2,2-tribromoethoxycarbonyl, alloxycarbonyl, benzyloxycarbonyl, 4-nitrophenylethoxycarbonyl, trichloromethylthiocarbonyl, or trichloroethoxycarbonyl.

7. The process of claim 6, wherein Y is trichloroethoxycarbonyl.

8. A process for synthesizing monosialoganglioside GM2, comprising:

(a) reacting a compound of formula:

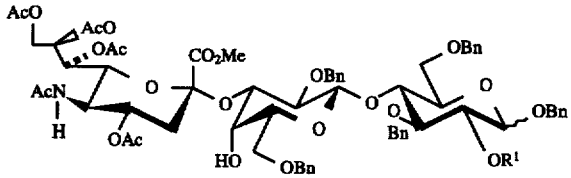

wherein R¹ is benzyl or pivaloyl, with a compound of formula:

with a compound of formula:

wherein R is ethyl, and Y is an electron withdrawing group, to form:

(c) replacing said electron withdrawing group by an acetyl group,
(d) removing any O-benzyl groups from the compound formed in (c),
(e) O-acetylating the compound formed in (d), and
(f) converting the compound formed in (e) to GM2.

9. The process of claim 8, wherein said electron withdrawing group is 2,2,2-trichloroethoxycarbonyl, 2,2,2-tribromethoxycarbonyl, 2,2,2-trifluoroethoxycarbonyl, or 4-nitrophenylethoxycarbonyl.

10. The process of claim 8, comprising replacing said electron withdrawing group with acetyl, by treatment in situ with zinc in acetic anhydride.

11. A process for synthesizing a monosialoganglioside GM2, comprising:

(a) reacting a compound of formula:

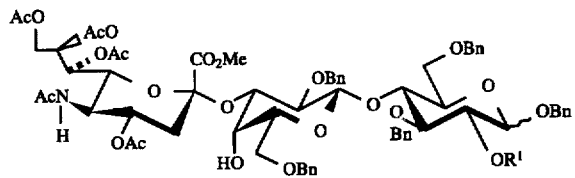

wherein $R^1$ is benzyl or pivaloyl, with a compound of formula:

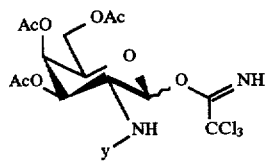

wherein Y is an electron withdrawing group, (b) replacing said electron withdrawing group by an acetyl group, (c) removing any O-benzyl groups from the compound formed in (b), (d) O-acetylating the compound formed in (c), and (e) transforming the compound formed in (d) to GM2.

12. The process of claim 11, wherein Y is: 2,2,2-trichloroethoxycarbonyl, 2,2,2-tribromoethoxycarbonyl, 2,2,2-trifluoroethoxycarbonyl, or 4-nitrophenylethoxycarbonyl.

13. The process of claim 11, wherein said electron withdrawing group is 2,2,2-trichloroethoxycarbonyl.

14. The process of claim 11 comprising removing said electron withdrawing group by treating said compound in situ with zinc in acetic anhydride.

15. The process of claim 11, wherein Y is a tribromoacetyl group, a trichloroacetyl group, or a trifluoroacetyl group.

16. The process of claim 15, wherein Y is a trichloroacetyl group.

* * * * *